US005662679A

United States Patent [19]

Voss et al.

[11] Patent Number: 5,662,679

[45] Date of Patent: Sep. 2, 1997

[54] TRAGUS ACUPRESSURE CLIP WITH OVER-OPENING PREVENTION AND PRESSURE ADJUSTMENT

[75] Inventors: Theodore N. Voss; Karl D. Kirk, III, both of New York, N.Y.

[73] Assignee: Shatzu Health Products, Inc., New York, N.Y.

[21] Appl. No.: 625,516

[22] Filed: Mar. 26, 1996

Related U.S. Application Data

[63] Continuation-in-part of Ser. No. 343,014, Nov. 21, 1994, abandoned, which is a continuation-in-part of Ser. No. 994,195, Dec. 21, 1992, Pat. No. 5,366,475.

[51] Int. Cl.[6] .................................................... A61B 17/00

[52] U.S. Cl. ......................... 606/204; 606/157; 606/151

[58] Field of Search .................................... 606/204, 206, 606/207, 201, 157, 151, 158, 205

[56] References Cited

U.S. PATENT DOCUMENTS

| | | | |
|---|---|---|---|
| 3,456,262 | 7/1969 | Coon | 24/511 |
| 3,923,064 | 12/1975 | Leupold | 606/204 |
| 4,122,852 | 10/1978 | Knetsch et al. | 606/204 |
| 4,319,574 | 3/1982 | Sun et al. | 606/204 |

FOREIGN PATENT DOCUMENTS 2 466 244 10/1995 France .

*Primary Examiner*—Michael Powell Buiz
*Assistant Examiner*—Kevin Truong
*Attorney, Agent, or Firm*—Meltzer, Lippe, Goldstein, et al.

[57] ABSTRACT

A tragus acupressure clip is disclosed with a concave spring having two opposing jaws. The jaws are separated by an opening of a slot delineated by an inner surface of the concave spring. Two opposing pressure pads are provided, each positioned on an inner surface of the concave spring and separated by the slot. Two mutually non-touching finger tabs are provided, each having one end attached to a different jaw on the outer surface of the spring. Each finger tab has a second end extending along an outer surface of the spring approximately only as far as the portion of the spring opposite the opening separating the jaws. When the second ends of the finger tabs are urged towards each other, against a compression bias of the spring, the slot separating the pressure pads is enlarged. The tragus acupressure clip is not subject to over-opening of the slot which over-opening would otherwise permanently deform the spring. According to another embodiment, one of the pads is attached to its respective clamping jaw via a threaded shaft so as to enable adjustment of the clamping pressure delivered by the clip.

8 Claims, 6 Drawing Sheets

TRAGUS ACUPRESSURE CLIP WITH OVER-OPENING PREVENTION AND PRESSURE ADJUSTMENT

RELATED PATENTS AND PATENT APPLICATIONS

This application is a continuation in part of U.S. patent application Ser. No. 08/343,014, entitled "Tragus Acupressure Clip with Over-Opening Prevention," filed on Nov. 21, 1994 now, abandoned for Theodore Voss and Karl D. Kirk, III, which is a continuation in part U.S. patent application Ser. No. 07/994,195 entitled "Tragus Acupressure Clip" filed for Theodore Voss, Barbara Curran, Karl D. Kirk III and Ellen Cohen on Dec. 21, 1992, now U.S. Pat. No. 5,366,475 issued on Nov. 22, 1994.

FIELD OF THE INVENTION

The present invention relates to acupressure devices. More particularly, the present invention relates to an ear clip which is placed on the tragus lobe of the ear in order to stimulate nerve endings.

BACKGROUND OF THE INVENTION

Acupressure, i.e., the application of pressure to specific topical locations of the body, has been used to control weight loss and to reduce the urge to smoke. It has been proposed that the application of light pressure to the tragus lobe (small cartilage lobe which partially eclipses the opening to the ear canal) slows peristalsis (the wave-like contractions of the intestine). The brain, in turn, may interpret this effect as being caused by a half full stomach. Thus, appetite is reduced. The control of the desire to smoke is less well understood.

The prior art has proposed acupressure ear clips. One ear clip is disclosed in a brochure distributed by Health Care Research, a company located in Patterson, N.J. This ear clip is designed to be secured to the auricle (the external cartilage portion of the ear which projects from the head). A second ear clip is disclosed in a 1990 brochure distributed by Nulife Corp. The Nulife clip is designed for attachment to the tragus and has a single padded arm which is positioned in the ear canal. A third "Chinese Weight Loss Earring" is disclosed in a 1992 "Mail Order Fun" catalogue distributed by the Johnson Smith Company located in Bradenton, Fla. The weight loss earring is an approximately circular shaped plastic device which fits loosely around the auricle and which may be manually squeezed periodically (using the fingers) to pinch the auricle. A fourth is disclosed in a March, 1994 advertisement distributed by Slim-Line products of Norcross Ga. This ear clip does not stimulate the ear by applying clamping pressure thereto but rather provides a small electric charge for stimulating the ear.

U.S. Pat. No. 4,319,574 (Sun) teaches an acupressure clip including an approximately circular assembly to which a spring may be attached. The circular assembly has a gap at which two clamping members are provided. One clamping member has a small surface area for applying stimulating pressure and the other clamping member has a large surface area at which no stimulating pressure is provided. The Sun device is designed for stimulating pressure points on the auricle, not the tragus lobe. Furthermore, the Sun device is difficult to place on the ear because it has no features for easy handling.

French Patent Document No. 2 466 244 shows a variety of clips. FIG. 4 of this reference shows a clip which has an approximately circular shaped clamp body. A gap is provided in the circular shaped clamp body with pads attached on opposite sides of the gap. Two lever arms are provided for widening the gap. These lever arms are positioned on the outer circumference of the circular shaped clamp body. The lever arms begin (i.e., are attached to) a portion of the circular shaped clamp body opposite the gap and extend approximately radially outwardly from the circular clamp body so that the distance from the gap to the far ends of the lever arms is much greater than the distance from the gap to the portion of the circular clamp body, to which the lever arms begin (i.e., are attached). This design, while allowing simple attachment to the ear is disadvantageous since the ends of the lever arms protrude much further from the clamp body than the portion of the clamp body opposite the gap. As such, the lever arm ends may contact other portions of the ear causing discomfort or even pain. Such a clamp may not be suitable for use while simultaneously using any other device which fits over or covers the ear such as a telephone receiver, ear muff, etc.

FIGS. 1*a*, 1*b* and 1*c*, show a tragus clip 1 according to related patent U.S. Pat. No. 5,366,475. The tragus clip 1 includes a concave spring 2 having jaws 3 and 4. The spring 2 has an outer concave surface portion 25 on which graphic or textual information, such as a company logo, may be printed. Two pressure pads 5 and 6 are positioned on an inner, concave surface of the spring 2 at the end 31 or 41 of each jaw 3 or 4, respectively. The tragus clip 1 also has finger tabs 7 and 8 connected on one end 71 or 81 to the end 31 or 41 of the jaws 3 or 4, respectively, on an outer, convex surface of the spring 2. In an illustrative embodiment, however, the finger tabs may be omitted. The finger tabs 7 and 8 are attached so that they extend away from the opening 9 approximately along the outer surface of the spring 2 or at an acute angle therewith.

Each finger tab 7 or 8 functions as a lever for widening the opening 9 of a slot 10 delineated by the inner, concave surface of the spring 2. The second ends 72 and 82 are grasped between thumb and forefinger and squeezed together. This causes the first ends 71 and 81 to displace away from one another. Since the first ends 71 and 81 are connected to the jaws 3 and 4, respectively, the jaws 3 and 4 separate, against the bias of the spring 2. Thus, the opening 9, separating the pressure pads 5 and 6, is widened. While in this "open" state, the tragus clip 1 is manipulated so that the tragus of the ear is inserted through the opening 9 into the slot 10, i.e., with one jaw (e.g., the jaw 3) positioned over the ear canal side of the tragus lobe and the other jaw (e.g., the jaw 4) positioned over the outer side of the tragus lobe. Once properly positioned, the pressure on the ends 72 and 82 of the finger tabs 7 and 8 is released. A restoration compression force of the spring 2 acts to press the jaws 3 and 4 together thereby causing the pressure pads 5 and 6 to clamp or pinch the tragus lobe.

In normal use, a tragus clip 1 is worn on each ear at the same time. Illustratively, the tragus clips are worn for up to three hours at a time.

The tragus acupressure clip 1 is advantageous because it is easy to attach to the tragus, because it supplies sufficient pressure to remain attached to the tragus yet is comfortable for use by a large segment of the population and because it is easy to manufacture. However, the clip 1 may be subject to over-opening. That is, it is possible for a user to pinch together finger tabs 7 and 8 so that the concave spring 2 opens beyond its threshold of elasticity. When this happens, the concave spring 2 permanently deforms in a configuration which is open too far. If the concave spring 2 is so deformed, it may not deliver sufficient clamping pressure to stimulate the tragus nerves or to even stay clamped to the tragus lobe.

Another issue associated with the use of the ear clip 1 is that the user may wish to adjust the amount of pressure delivered by the ear clip. For instance, the user may be more sensitive initially but may later develop a tolerance for more pressure. Alternatively, more pressure may be desired to ensure that the clip does not fall off.

It is an object of the present invention to overcome these problems.

SUMMARY OF THE INVENTION

These and other objects are achieved by the present invention. According to one embodiment, a tragus acupressure clip is provided with a concave spring having two opposing jaws. The jaws are separated by an opening of a slot delineated by an inner surface of the concave spring. Two opposing pressure pads are provided, each positioned on an inner surface of the concave spring and separated by the slot. Two finger tabs are provided which do not touch when the spring is in a state of rest. Each finger tab has one end attached to a different jaw on the outer surface of the spring. Each finger tab has a second end extending along an outer surface of the spring approximately only as far as the portion of the spring opposite the opening separating the jaws. When the second ends of the finger tabs are urged towards each other, against a compression bias of the spring, the slot separating the pressure pads is enlarged.

Over-opening of the spring may be prevented in a number of ways. For instance, the spring may be made from a high yield tempered stainless steel. Alternatively, the finger tabs may be provided with a bend to angle back the second ends towards each other so that they meet, or so that the finger perchace thereon is limited. In either case, the user is prevented from urging the finger tabs towards each other to open the spring beyond is elastic limit. In yet another alternative embodiment, the spring is formed by two nested springs, which construction increase the elastic limit of the spring.

In another embodiment, the ear clip is designed so that at least one pad may be adjustably moved closer to the other pad to narrow the slot. For instance, one pad may be mounted to a threaded shaft which engages a threaded hole formed through the respective clamping jaw (e.g., the hole extending in the direction of the separation between the two pads). By rotating the pad, the threaded shaft withdraws towards the threaded hole in the jaw (thereby widening the slot) or extends from the threaded hole (thereby narrowing the slot) so as to adjust (i.e., increase or decrease) the clamping pressure delivered by the pads.

DETAILED DESCRIPTION OF THE INVENTION

Prior to discussing the embodiments according to the present invention, some details regarding the construction of the tragus acupressure clip disclosed in U.S. Pat. No. 5,336,475 (shown in FIGS. 1*a–c*, 2*a–b*, 3*a–b*, 4*a–b* and 5*a–b*) are reviewed in section I. Then, in section II, a tragus clip with over opening prevention according to an embodiment of the present invention is described. Section III describes a tragus clip with pressure adjustment according to another embodiment of the present invention.

I. Basic Tragus Clip

The tragus clip 1 applies a clamping force to the tragus lobe, thereby affixing the clip to the tragus lobe and stimulating nerve endings thereat. The amount of force developed by the tragus clip 1 depends on its dimensions, the materials used in its construction and the size of the tragus lobe to which the tragus clip 1 is attached. It is important to design the tragus clip 1 so that it delivers the correct amount of force. If too little force is applied by the tragus clip 1, it may tend to slip off the tragus. On the other hand, too much force can readily cause headaches, queazy stomachs and sore ears.

The tragus clip 1 is illustratively designed to deliver a different clamping force in the range of approximately 0.05 to 0.20 lbs. Different users of the tragus clip 1 can tolerate different levels of force on their tragi. Some users cannot tolerate any force, no matter how light, while others can tolerate up to 0.2 lbs. of force. Illustratively, the tragus clip 1 is designed to deliver 0.17 lbs. of clamping force as this level of force can be tolerated by a large segment of the population. When compressed, the tragus is approximately 0.125" thick with a $5^{th}$ to $95^{th}$ percentlie range of 0.106" to 0.141". Additionally, men, older people and overweight people have slightly, but significantly, thicker tragi. Illustratively, the tragus clip 1 is designed to deliver the same clamping force, e.g., 0.10 lbs, to the tragus over a broad range of jaw separations, which jaw separations are caused by different tragus thicknesses.

Figure 2A:
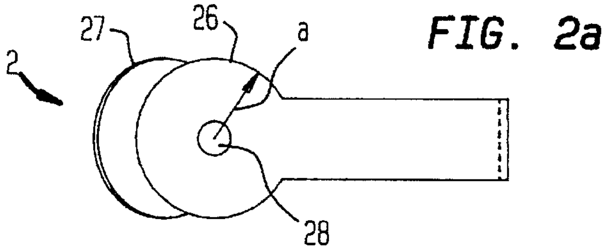
FIGS. 2*a* and 2*b* show a side and top view, respectively, of a spring of the embodiment depicted in FIG. 1 in greater detail.
Figure 2B:
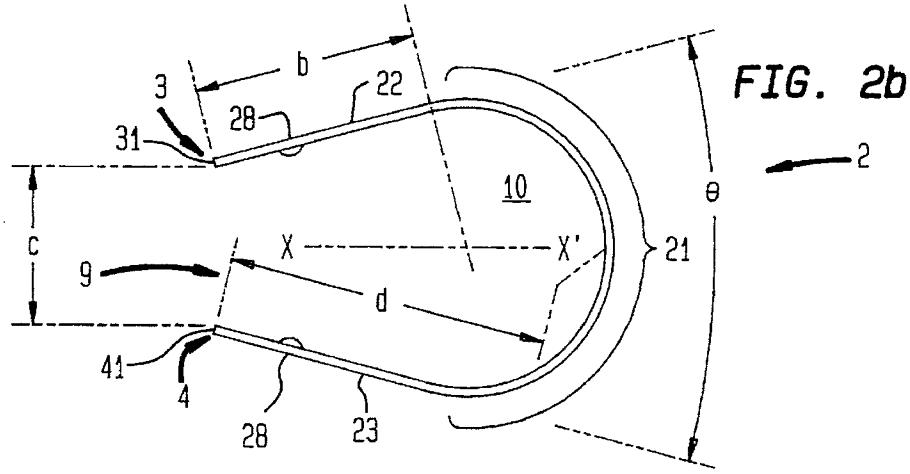

Turning now to FIGS. 2*a* and 2*b*, the spring 2 is shown in greater detail. Illustratively, the spring 2 is made out of stainless steel; however, any elastic material can be used which generates the requisite force over the range of deflections produced by the expected rage of tragus thicknesses. Stainless steel also offers an advantage in that it is easy to form.

Illustratively, the spring 2 is formed from a flat blank approximately 1.118" in length. In FIG. 2*b*, d=0.451". The blanks may have enlarged, approximately circular plates 26 and 27 on which the pads 5 and 6 (FIGS. 1*a–c* and 4*a–b*) may be affixed. Illustratively, each plate has an a=0.118" radius. The spring 2 may also have welding dimples 28 and 29 for locating a welding point for affixing the finger tabs 7 and 8 (FIGS. 1*a–c* and 3*a–b*).

As shown, the blank is illustratively formed into a "C" shape having an axis of symmetry XX'. A "C" shape provides the simplest, most economical use of material and yields a spring with a fairly flat force-to-deflection curve over the range of installed deflections typically experienced by the spring 2.

As depicted, the "C" shaped spring 2 illustratively has an approximately semi-circular portion 21 with a radius of curvature in the range of approximately 0.12 to 0.20", e.g., the radius of curvature may be 0.16". The jaws 3 and 4 are formed by arms 22 and 23 which extend from the ends of this semi-circular portion 21 approximately b=0.260" along the rays of an approximately Θ=29° angle. The vertex of this angle is illustratively positioned outside the slot 10 on the axis of symmetry XX', at least some distance from the opening 9. The vertex, however, is closer to the opening 9 than the semi-circular portion 21 of the spring 2. The ends of each jaw 31 and 41 are separated by approximately c=0.205" in a state of rest. Illustratively, these jaws 31 and 41 may be designed so that they are separated by anywhere from approximately 0.0 to 0.25" in a state of rest. Furthermore, the spring 2 is illustratively designed so that the ends 31 and 41 may be displaced up to a approximately 0.35" separation without permanent deformation. Illustratively, the jaw ends 31 and 41 are displaced up to an approximately 0.275" separation during use.

The width, thickness, material and temper of the spring 2 can vary over a large range but the overall physical size, specifically, the radius of curvature of the semi-circular portion 21 and length of the arms 22 and 23, cannot. This is because large sized "C" shaped springs 2 would be obtrusive in a petite ear, while small sized "C" shaped springs 2 may not fit around large tragi.

Figure 3A:
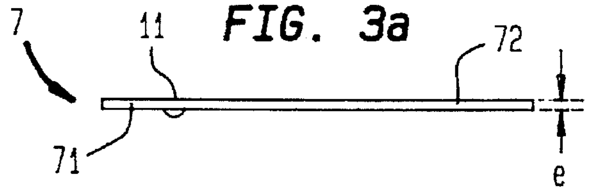
FIGS. 3*a* and 3*b* show a side and top view, respectively, of a finger tab of the embodiment depicted in FIG. 1 in greater detail.
Figure 3B:
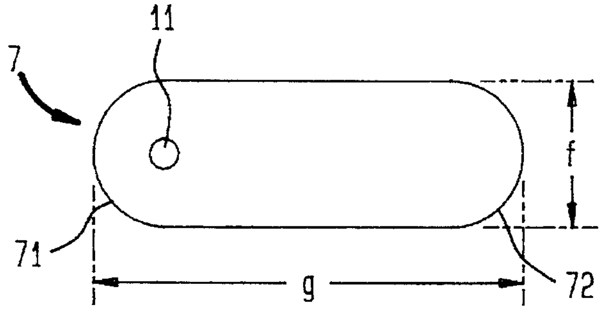
Figure 5A:
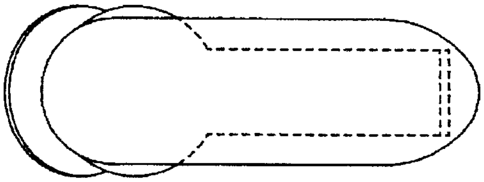
FIGS. 5*a* and 5*b* show a side and top view of an integral spring and finger tab construction of another embodiment of U.S. Pat. No. 5,366,475.
Figure 5B:
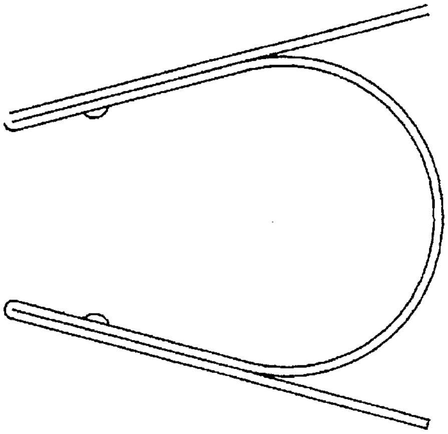

Referring now to FIGS. 3*a* and 3*b*, a finger tab, e.g., the finger tab 7, is shown. As shown, the finger tab 7 is a separate stainless steel piece which is spot welded, at the welding point 11, to the welding dimple 28 or 29 on the outer concave surface of the spring 2 (FIGS. 1*a–c* and 2*a–b*). This is only illustrative, however. In the alternative, the finger tab 7 may be made of another material, such as plastic, and may be attached in another fashion, such as by gluing. In yet another alternative embodiment, the finger tabs 7 and 8 and the spring 2 are integral which integral unit may be formed from a single flat stainless steel blank as shown in FIGS. 5*a* and 5*b*.

Figure 1A:
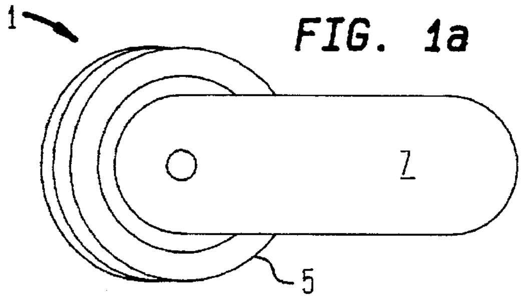
FIGS. 1*a*, 1*b* and 1*c* show a side, top and rear view, respectively, of an embodiment of a tragus clip of U.S. Pat. No. 5,366,475.
Figure 1B:
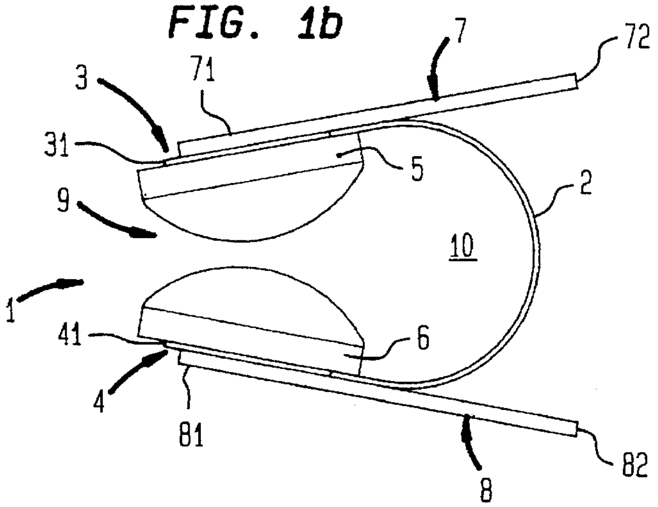
Figure 1C:
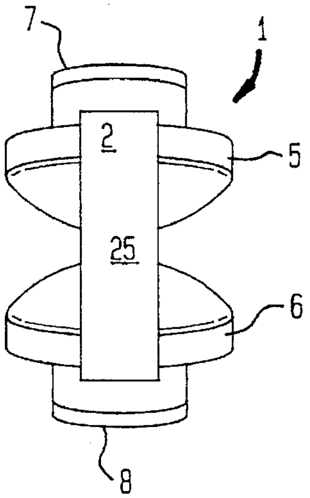

The dimensions of the finger tabs 7 and 8 can vary greatly. A larger finger tab 7 or 8 provides greater control while it is pinched between thumb and forefinger. However, a smaller finger tab 7 or 8 can fit entirely in the ear canal without touching it. This allows the user to speak on the telephone without having to first remove the tragus clip 1 (FIGS. 1*a–c*). A diamond knurling pattern may also be added to improve finger perchance on the finger tabs 7 and 8.

Illustratively the finger tab 7 is a flat rectangular plate with semicircular ends 71 and 72. For example, the tab 7 may be g=0.45" long, f=0.15" wide, e=0.015" thick and have semi-circular ends with a radius of 0.075".

Figure 4A:
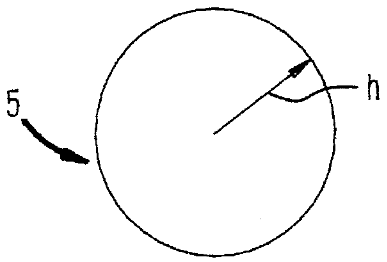
FIGS. 4*a* and 4*b* show a top and cross-sectional view, respectively, of a pressure pad of the embodiment shown in FIG. 1 in greater detail.
Figure 4B:
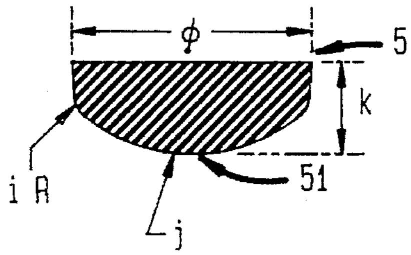

Referring now to FIGS. 4*a* and 4*b*, a pressure pad, e.g., the pressure pad 5, is shown in greater detail. The pressure pad 5 is illustratively secured to the jaw 3 (FIGS. 1*a* and 2*b*), for example, to the inner surface of the plate 26 (FIG. 2*a*), using a bonding agent such as Loctite 401.

The diameter, profile and softness of the pressure pad 5 all interplay to render a comfortable interface to the ear. The durometer of the material used to form the pressure pad 5 has the greatest impact on comfort. Illustratively, a material with a durometer in the range of 5 Shore A to 12 Shore A may be used. Materials below 5 Shore A in softness are too difficult to handle and too pliable to provide a uniform distribution of the pinching force of the spring 2 (FIGS. 1*a–c* and 2*a–b*). Harder materials having a durometer above 12 Shore A do not readily conform to the variations in tragus contour and therefore develop "hotspots" of discomfort. Illustratively, an elastomeric material having a 6 Shore A durometer, such as PMC-724 castable urelastomer, is used.

The spherical radius profile 51 of the pressure pad 5 provides for a normalized transfer of force from the spring 2 (FIG. 1*a–c*) regardless of the mount of deflection of the spring 2 (FIGS. 1*a–c*), or variations in the tapered contour of the tragus, between its interior and exterior surfaces. Illustratively, the spherical radius profile 51 has a j=0.180" spherical radius.

As depicted, the spherical radius profile 51 illustratively extends from a tapered cylinder, or base portion of an approximately conical cross-section having a Φ=4° angle. The zenith of the spherical profile extends k=0.095" above the bottom of the pressure pad 5, which bottom is affixed to the inner surface of the spring 2 (FIGS. 1*a–c*).

The diameter of the pressure pad 5 is chosen to be in the range of approximately h=0.18" to 0.38". A larger pressure pad 5 would entirely cover most tragus lobes but could not be securely attached to a small tragus. Furthermore, a larger pressure pad 5 would require a heavier spring 2 (FIGS. 1*a–c* and 2*a–b*) in order to maintain consistent pad pressure, which heavier spring 2 (FIGS. 1*a–c* and 2*a–b*) would encroach on the comfort of the user. On the other hand, a smaller radius pressure pad 5 would not be as effective in stimulating nerve endings on a larger tragus. Furthermore, a smaller pressure pad 5 would require a lighter spring 2 (FIGS. 1*a–c* and 2*a–b*) in order to maintain a consistent pad pressure, which lighter spring 2 may compromise the ability of the tragus clip 1 (FIGS. 1*a–c*) to remain affixed to the tragus. Illustratively, the pressure pad 5 has an i=0.250" radius.

II. Tragus Acupressure Clip with Over-Opening Prevention

As mentioned above, an illustrative basic clip 1 is described for which the ends 31 and 41 of a concave spring 2 may be opened or separated up to 0.35" without permanently deforming the concave spring 2. However, the ends 72 and 82 of the finger tabs 7 and 8 may be pinched together so as to open the concave spring 2 more the than 0.35" This tends to permanently deform the concave spring 2 in an open position which reduces the clamping force supplied by the clip 1. The reduced clamping force may not be sufficient to stimulate the tragus lobe or to even keep the clip 1 attached to the lobe. This problem may be remedied according to the present invention as described below.

A. High-Yield, Tempered Stainless Steel

The concave spring 2 of the tragus acupressure clip 1 may be manufactured from a high yield tempered stainless steel. A standard 301 spring steel may be used with a special high yield tempering to improve its physical properties. Such a clip has the same dimensions as discussed above. The properties of the concave spring 2 are as follows: a minimum tensile strength of 270,00 psi and a minimum yield strength of 269,000 psi. Any materials with properties that meet or exceed these physical parameters would be acceptable.

B. Finger Tabs With Meeting Edges

Figure 6A:
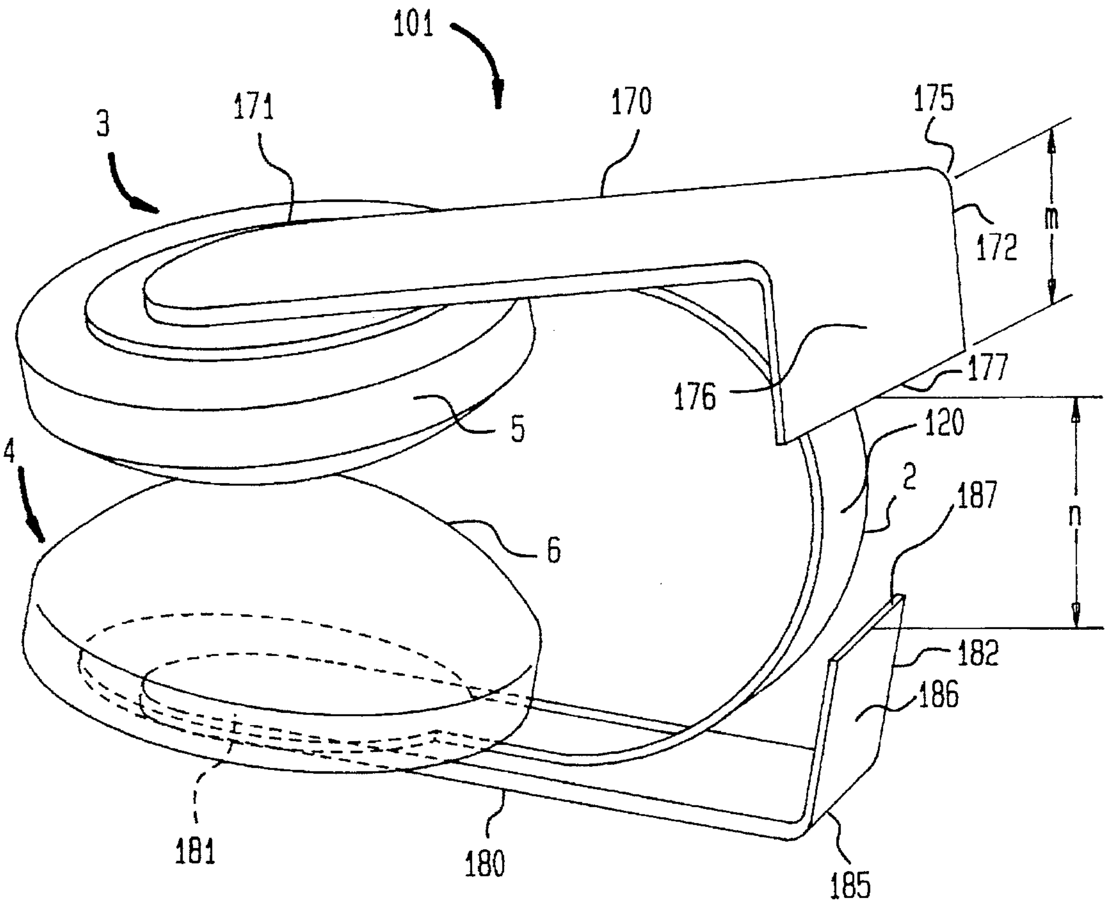
FIGS. 6*a* and 6*b* show an isometric and side view of a tragus acupressure clip according to a first embodiment of the present invention.
Figure 6B:
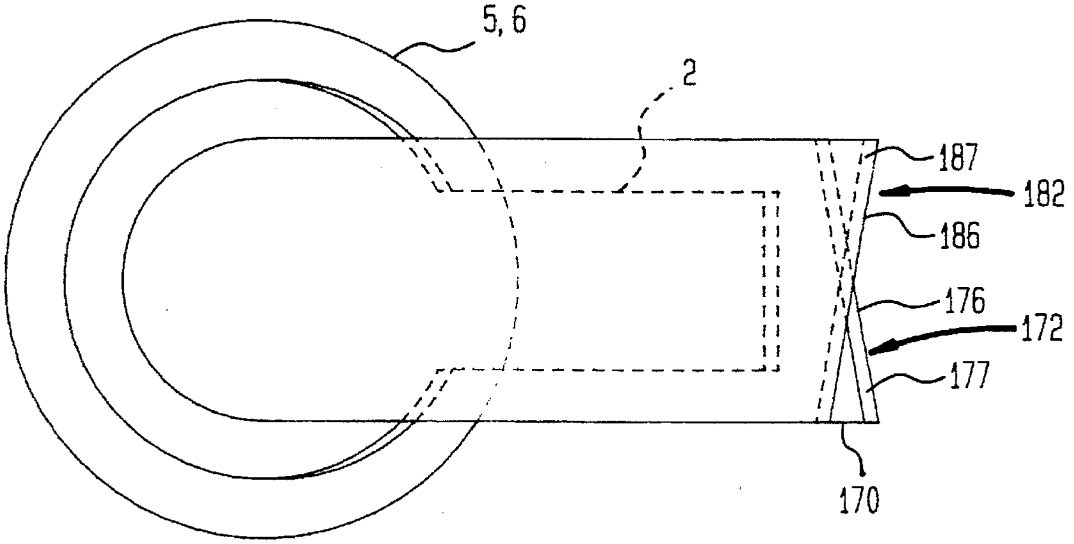

FIGS. 6*a–b* show another embodiment 101 of the present invention. Like parts are labelled with the same numerals. As shown, each finger tab 170 and 180 has a bend 175 or 185 between the first end 171 or 181 connected to the jaw 3 or 4 and the second end 172 or 182. The second ends 172 and 182 are bent towards each other so that as they are urged towards each other, edges 177 and 187 thereof meet. (Advantageously, back stops 176 and 186 are formed as close as possible to the rear portion 120 of the spring 2 so that they do not intrude on the auricle.) The meeting of the edges 177 and 187 prevents the user from further opening the concave spring 2 beyond a predetermined limit (which limit is selected to be less than he elastic limit of the spring so as to prevent permanent deformation). As shown in FIG. **6*b*, the ends 182 and 172 are advantageously twisted with respect to each other to ensure that edges 177 and 187 meet. Advantageously, the backstop portions 176 and 186** extend approximately m=0.2" each in a direction towards each other and, in a state of rest, are separated by about n=⅛".

C. Perchace Limiting Finger Tabs.

Figure 7:
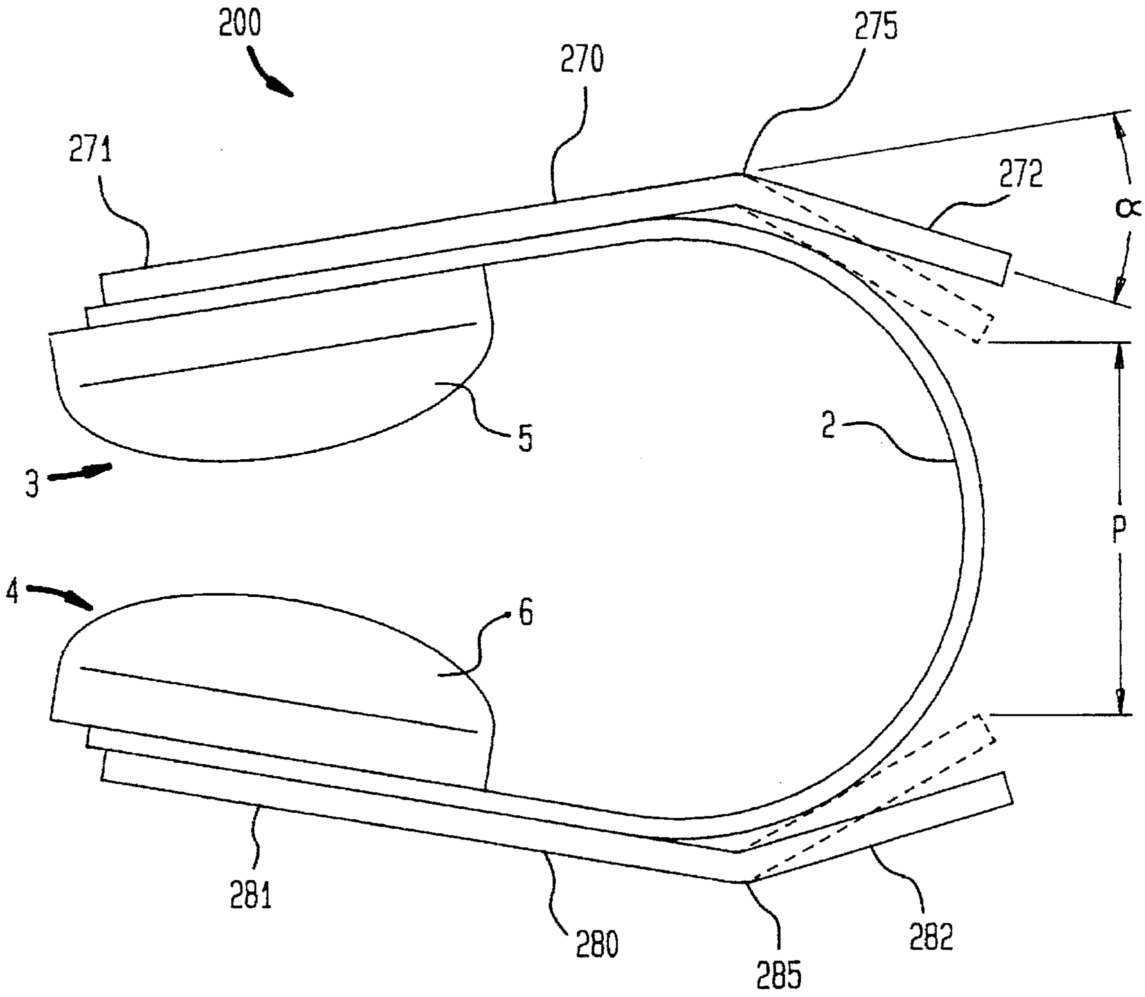
FIG. 7 shows a top view of a tragus acupressure clip according to a second embodiment of the present invention.
Figure 8A:
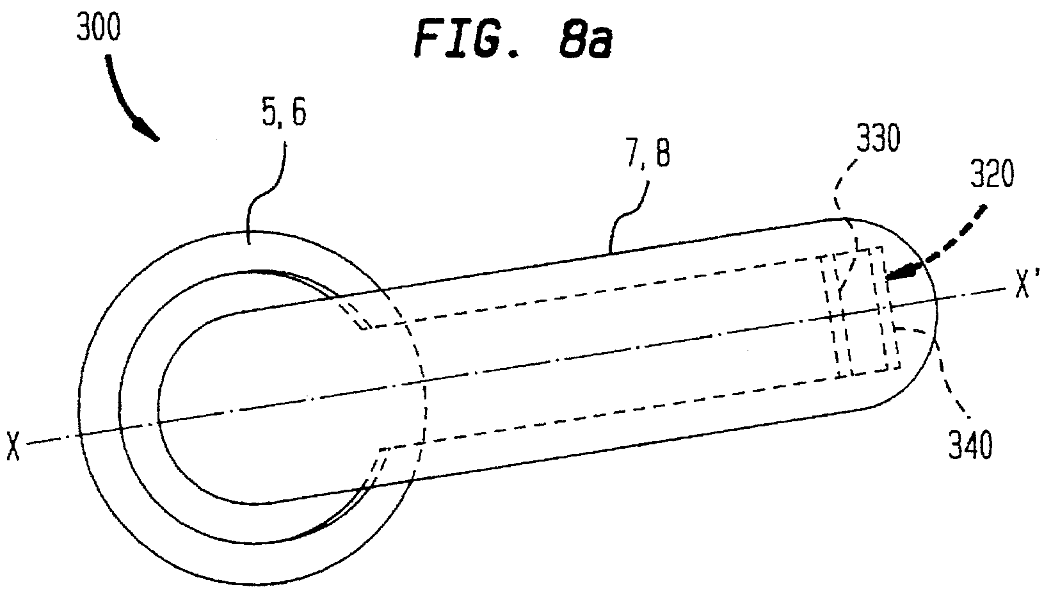
FIG. 8*a* and 8*b* show a side and top view of a tragus acupressure clip according to a third embodiment of the present invention.
Figure 8B:
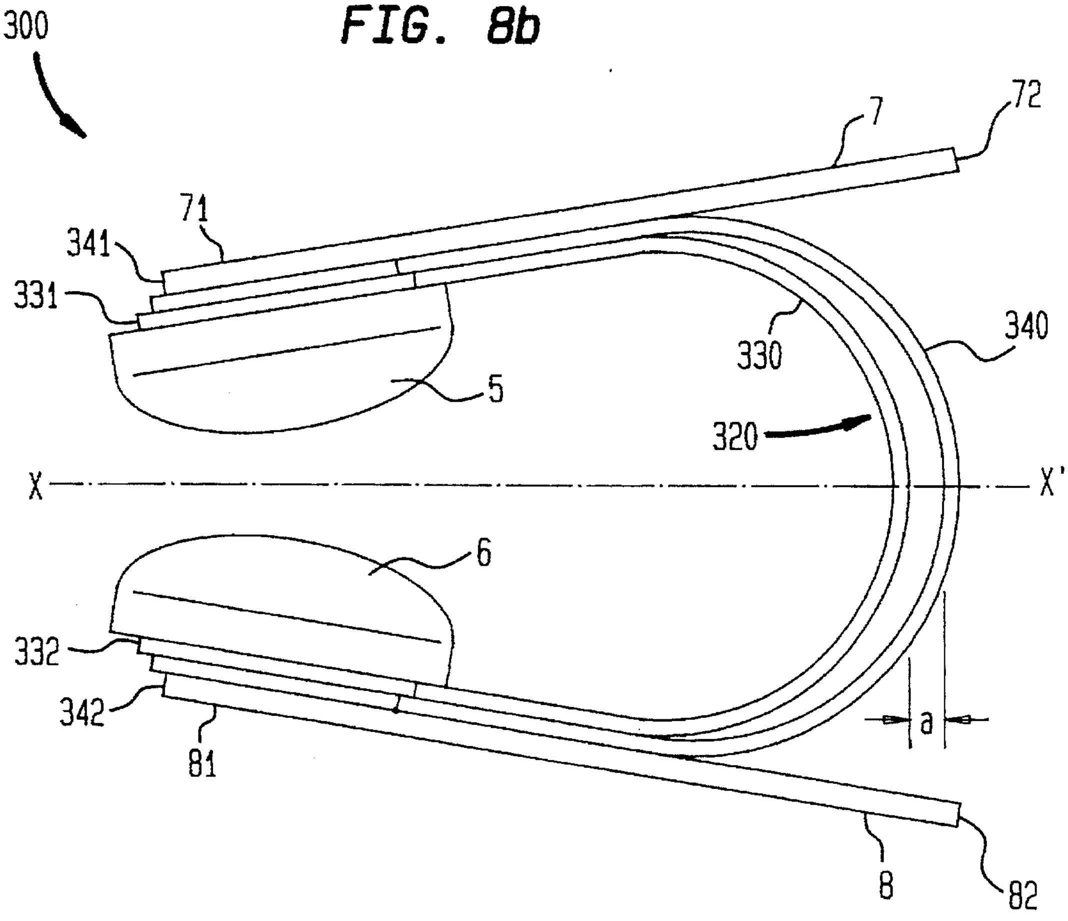
Figure 9A:
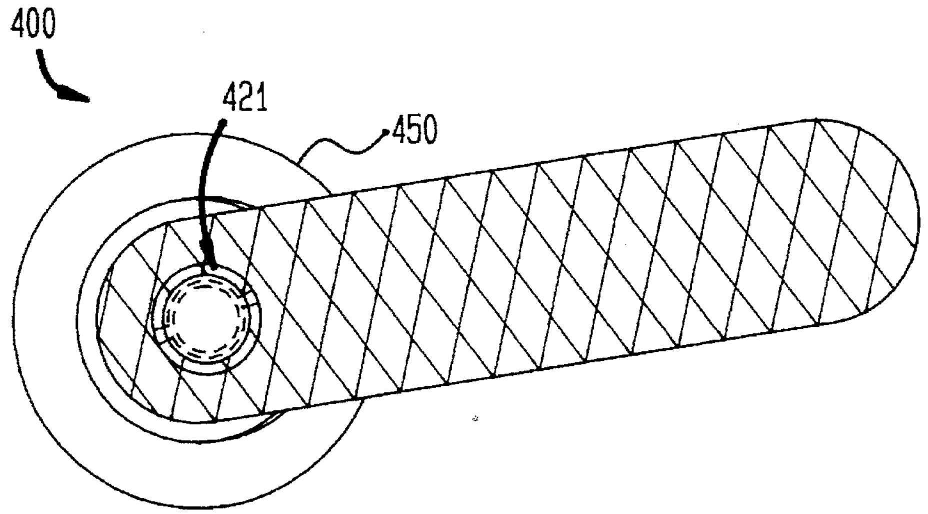
FIGS. 9*a* and 9*b* show a side and top view of a tragus acupressure clip according to a fourth embodiment of the present invention.
Figure 9B:
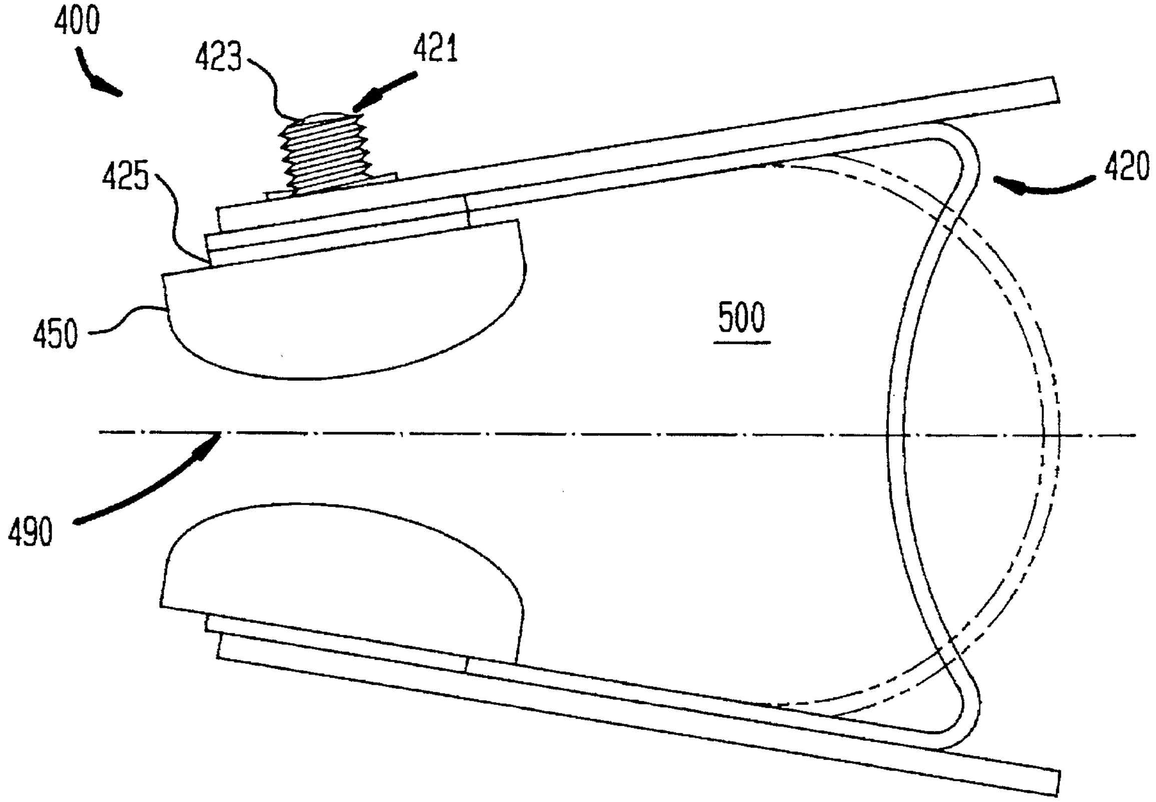

FIG. 7 shows a second tragus acupressure clip embodiment 200 to prevent over opening. Like the embodiment of the clip 100, each finger tab 270 and 280 has a bend 275 or 285 between the first end 271 or 281 and the second end 272 or 282.

However, the finger tabs 270 and 280 are bent only about $\alpha$=5°–20° (with ends 272 and 282 bent towards each other) at about the midpoint of each tab 270 or 280. This limits the perchace, or ability to manually grip the clip 200 at the finger tabs 270 and 280 as the second ends 272 and 282 are urged towards each other. In particular, the angle $\alpha$ is chosen to prevent over-opening the concave spring 2. That is, as the user urges ends 272 and 282 towards each other to over-open the concave spring 2, the user suddenly loses grip of the clip 200 which tends to eject from the user's finger tips. Illustratively, the urging of the finger tabs 270, 280 is limited to a p=⅜" deflection of the second ends 272, 282.

D. Nested Concave Springs

Finally, FIGS. **8*a–b* show an embodiment 300 to prevent over opening of the concave spring 320. The concave spring 320 includes an inner spring 330 and an outer spring 340 connected together in a nested configuration. That is, the inner spring 330 is inserted into the slot of the outer spring 340 with their axes X–X' aligned, and both springs 330 and 340 are joined at their jaws 331–341 and 332–342. Advantageously, this permits thinning out each spring to a thickness of about q=0.0065". The thinning of the spring reduces the amount of stress experienced for a given deflection. This in turn raises the elasticity threshold. Thus, despite the user being able to open the concave spring 320** beyond 0.35", no permanent deformation occurs because the elasticity limit is not exceeded. However, thinning a spring reduces its restoration bias. Therefore, two springs are provided so that the requisite clamping force is generated.

III. Tragus Acupressure Clip with Pressure Adjustment

FIGS. **9*a–9b* show an embodiment of the tragus acupressure clip 400 which enables adjustment of the amount of clamping pressure that is delivered by the clip 400. As shown, a threaded shaft 421 is provided which extends through the spring 420. The threaded shaft 421 has a first end 423 that engages threads of a hole formed through the spring 420 (and illustratively also through the finger tab 470). The threaded shaft has a second end 425 that extends into the opening 490 of the slot 500. The second end 425 of the shaft 421 is connected to the pressure pad 450. Illustratively the second end 425 of the threaded shaft 421 may have a flattened disc shape so as to provide a large surface onto which the pressure pad 450** may be mounted.

Illustratively, the threaded shaft 421 is a #2–32 threaded nylon post (with diameter of 1.0 cm or 0.40") with an adjustment travel (withdrawal from, or extension into, the opening 490 of the slot 500) of 0.1905 cm (0.075"). In operation, the user may rotate the pad 450 to withdraw or extend the threaded shaft 421 thereby narrowing or widening the opening 490. The extension of the threaded shaft 421 and attached pad 450 into the opening 490 tends to increase the amount of clamping pressure applied by the clip 400 to the tragus. Such additional pressure can be used to vary the pressure depending on the sensitivity of each individual user or increase pressure as the user becomes more accustomed to using the clip 400. Additionally, increasing pressure can counteract spring 420 distortion attributed to manufacturing tolerances, or use (in the case that the spring 420 is made from a material subject to deformation by repeated use). In a like fashion, withdrawal of the threaded shaft 421 and attached pad 450 from the opening tends to decrease the amount of clamping pressure applied by the clip 400 to the tragus.

Note also that the spring 420 can have an inverted arch shape so that the spring 420 shape is convex. Such a shape is easier to manufacture since the metal blank must be bent beyond its yield point to form such a shape, thereby ensuring that the blank will be permanently deformed into the correct shape to produce the requisite clamping pressure.

Finally, the aforementioned discussion is intended to be merely illustrative. Numerous other embodiments of the present invention may be devised by those having ordinary skill in the art without departing from the spirit or scope of the following claims.

We claim:

1. A tragus acupressure clip which prevents over-opening comprising:

a concave spring having two opposing jaws separated by an opening of a slot delineated by an inner surface of said concave spring, two opposing pressure pads, each attached to the end of a different one of said jaws on said inner surface of said concave spring, and separated by said slot, two finger tabs, which are mutually non-touching when said spring is in a state of rest, each of said finger tabs having one end attached to the end of a different jaw, on an outer surface of said spring, and having a second end extending away from said end of said jaw, along an outer surface of said spring approximately only as far as a portion of said spring opposite to said opening of said slot separating said jaws, whereby said second ends of said finger tabs are urged towards one another, against a compression bias of said spring to enlarge said slot separating said pressure pads, and wherein each of said finger tabs comprises a bend between said first and second ends of said finger tabs so that said second ends are angled towards each other, said bend in said second ends of said finger tabs decreasing an ability to grip said second ends of said finger tabs as said second ends of said finger tabs are urged towards one another, said decrease in ability to grip said finger tabs limiting an opening of said slot beyond an elastic limit of said concave spring.

2. The tragus acupressure clip of claim 1 wherein said angle of said bend is in the range of 5°–20°.

3. A tragus acupressure clip which prevents over-opening comprising:

a concave spring having two opposing jaws separated by an opening of a slot delineated by an inner surface of said concave spring, two opposing pressure pads, each attached to the end of a different one of said jaws on said inner surface of said concave spring, and separated by said slot, two finger tabs, which are mutually non-touching when said spring is in a state of rest, each of said finger tabs having one end attached to the end of a different jaw, on an outer surface of said spring, and having a second end extending away from said end of said jaw, along an outer surface of said spring approximately only as far as a portion of said spring opposite to said opening of said slot separating said jaws, whereby said second ends of said finger tabs are urged towards one another, against a compression bias of said spring to enlarge said slot separating said pressure pads, and wherein each of said finger tabs comprises a bend between said first and second ends of said finger tabs so that said second ends are angled towards each other, said second ends of each of said finger tabs meeting as said finger tabs are urged towards one another to prevent urging said finger tabs towards each other beyond a certain limit so as to limit an opening of said slot beyond an elastic limit of said concave spring.

4. The tragus acupressure clip of claim 3 wherein meeting edges of said second ends of said finger tabs are twisted relative to one another.

5. A tragus acupressure clip comprising:

a concave spring having two opposing jaws separated by an opening of a slot delineated by an inner surface of said concave spring, two opposing pressure pads, each attached to the end of a different one of said jaws on said inner surface of said concave spring, and separated by said slot, two mutually non-touching finger tabs, each having one end attached to the end of a different jaw, on an outer surface of said spring, and having a second end extending away from said end of said jaw, along an outer surface of said spring approximately only as far as a portion of said spring opposite to said opening of said slot separating said jaws, whereby said second ends of said finger tabs are urged towards one another, against a compression bias of said spring to enlarge said slot separating said pressure pads, and wherein said concave spring is made of high yield tempered stainless steel.

6. A tragus acupressure clip comprising:

a concave spring including an inner concave spring positioned with an outer concave spring and attached thereto to define two opposing jaws separated by an opening of a slot delineated by an inner surface of said inner concave spring, two opposing pressure pads, each attached to the end of a different one of said jaws on said inner surface of said inner concave spring, and separated by said slot, two mutually non-touching finger tabs, each having one end attached to the end of a different jaw, on an outer surface of said outer concave spring, and having a second end extending away from said end of said jaw, along an outer surface of said spring approximately only as far as a portion of said outer concave spring opposite to said opening of said slot separating said jaws, whereby said second ends of said finger tabs are urged towards one another, against a compression bias of said concave spring to enlarge said slot separating said pressure pads.

7. A tragus acupressure clip with clamping pressure adjustment comprising:

a concave spring having first and second opposing jaws separated by an opening of a slot delineated by an inner surface of said concave spring, a threaded shaft having a first end disposed in a hole formed through said first clamping jaw and a second end extending into said opening, wherein a rotation of said shaft extends said second end into and withdraws said second end from, said opening of said slot, first and second opposing pressure pads, said first pressure pad being attached to said second end of said threaded shaft and said second pressure pad being attached to the end of said second jaw on said inner surface of said concave spring, said first and second pressure pads being separated by said slot, two finger tabs, which are mutually non-touching when said spring is in a state of rest, each of said finger tabs having one end attached to the end of a different jaw, on an outer surface of said spring, and having a second end extending away from said end of said jaw, along an outer surface of said spring approximately only as far as a portion of said spring opposite to said opening of said slot separating said jaws, whereby said second ends of said finger tabs are urged towards one another, against a compression bias of said spring to enlarge said slot separating said pressure pads.

8. The tragus acupressure clip of claim 7 wherein a rotation of said shaft in a first direction extends said first pad so as to narrow said slot and to increase a clamping pressure of said clip.

* * * * *